United States Patent [19]

Smith et al.

[11] Patent Number: 4,479,851

[45] Date of Patent: Oct. 30, 1984

[54] PURIFICATION OF VIDEO DISC LUBRICANT ADDITIVES

[75] Inventors: Thomas E. Smith, Indianapolis, Ind.; Chih C. Wang, Hightstown, N.J.

[73] Assignee: RCA Corp, New York, N.Y.

[21] Appl. No.: 440,452

[22] Filed: Nov. 10, 1982

[51] Int. Cl.$^3$ .......................... B01D 3/10; B32B 3/02
[52] U.S. Cl. ......................................... 203/80; 203/91; 203/DIG. 11; 428/64; 428/447; 556/450
[58] Field of Search ....................... 203/80, 91, 94, 88, 203/99, DIG. 11; 428/64, 447; 260/23 EP, 998.16; 252/27; 556/450

[56] References Cited

U.S. PATENT DOCUMENTS

| | | | |
|---|---|---|---|
| 2,405,393 | 8/1946 | Atkins | 203/DIG. 11 |
| 3,280,091 | 10/1966 | Dance | 203/80 |
| 3,364,731 | 1/1968 | Hook | 203/DIG. 11 |
| 3,428,530 | 2/1969 | Fauche et al. | 203/80 |
| 3,540,987 | 11/1970 | Garkisch et al. | 203/DIG. 11 |
| 3,625,835 | 12/1971 | Sittard | 203/80 |
| 4,228,050 | 10/1980 | Martin et al. | 260/23 |
| 4,275,101 | 6/1981 | Wang et al. | 369/286 |
| 4,355,062 | 10/1982 | Wang et al. | 428/64 |

*Primary Examiner*—Wilbur Bascomb
*Attorney, Agent, or Firm*—Birgit E. Morris; Howard F. VanDenburgh

[57] ABSTRACT

An improved process for the batch distillation or purification by stripping of a bis(hydroxyalkyl)disiloxane, which purified product is useful as a video disc lubricant additive or dopant. In accordance with the process, the feedstock of bis(hydroxyalkyl)disiloxane is subjected to a vacuum evaporation of the light volatiles by gradually reducing the pressure to about $2 \times 10^{-1}$ Torr. After the low boiling materials have been distilled off, the temperature is gradually increased and the pressure gradually reduced (final temperature of about 135° C. and final pressure of about $4 \times 10^{-2}$ Torr) so as to produce a distill and having a viscosity of about $210 \pm 30$ centipoise at 25° C.

5 Claims, 1 Drawing Figure

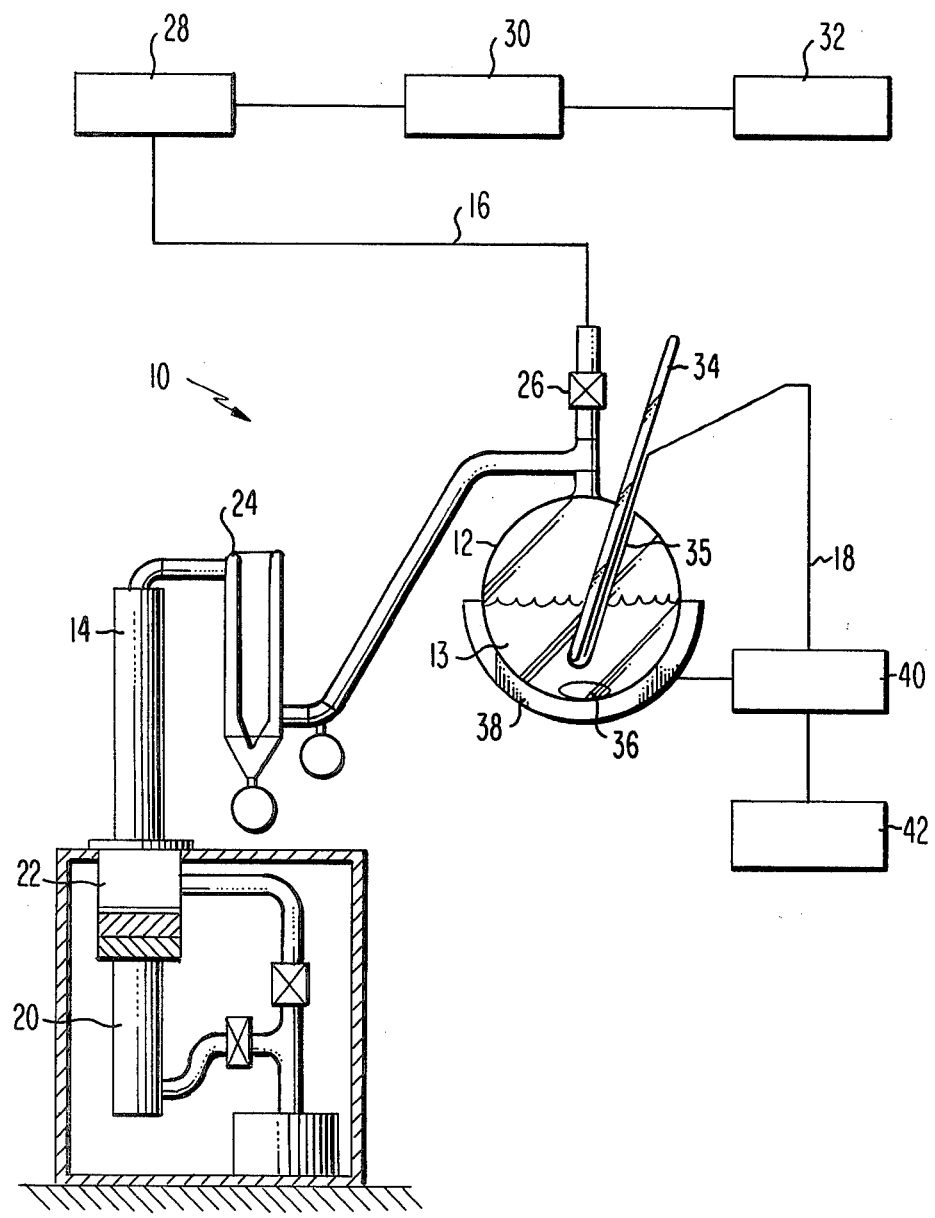

PURIFICATION OF VIDEO DISC LUBRICANT ADDITIVES

This invention relates to high density information disc lubricant additives. More particularly, the invention pertains to an improved process for purifying bis(hydroxyalkyl)disiloxane for use as a video disc lubricant additive or dopant.

BACKGROUND OF THE INVENTION

Wang et al, in copending U.S. application Ser. No. 231,859 filed Feb. 5, 1981 now U.S. Pat. No. 4,355,062 have disclosed a new class of bis(hydroxyalkyl)disiloxanes which are useful as additives or dopants for methyl alkyl siloxanes employed as lubricants for capacitive electronic discs. These additives or dopants are made by reacting dichlorodialkylsilanes with a heterocyclic ethylene oxide, such as tetrahydrofuran, heating the product in the presence of an alkali metal to form a 1-oxa-2-silacycloalkane, and hydrolyzing this last product in the presence of an acidic catalyst, such as HCl, to form a bis(hydroxyalkyl)disiloxane.

In order to successfully employ these disiloxane dopants or additives in lubricants for capacitive electronic disc manufacture, they must be highly purified, particularly to remove volatiles and other impurities that would change the chemical composition or the rheological properties of the doped lubricant on the surface of the disc with time. Accordingly, the dopant has heretofore, both commercially and as disclosed in U.S. application Ser. No. 231,859 now U.S. Pat. No. 4,355,062 referred to hereinabove, been molecularly distilled by the "falling film" type of molecular distillation at approximately 100° C. and about $2 \times 10^{-3}$ Torr to purify the dopant and to remove low molecular weight materials including HCl, alcohols and unreacted oxasilacycloalkanes.

However, molecular distillation, particularly of the "falling film" type which is presently commercially used and the type successfully employed in above-referred to U.S. application 231,859 now U.S. Pat. No. 4,355,062, is time consuming and expensive. This type of distillation can process only about 1½ liters of raw material per week, or one drop every 12 seconds; and requires close supervision because the temperature versus the pressure is very critical to obtain a good product. Additionally, the equipment must be carefully monitored for leaks since contamination from the atmosphere reaching the hot distilling liquid may result in thermal degradation of the product.

For a material to be useful as a capacitance electronic disc lubricant additive or dopant, it must meet very stringent specifications. These specifications require that the material have a molecular weight of approximately 530; a viscosity at 25° C. of 210±30 centipoises; less than 10 ppm of inorganic purities; must be free of particulates; must have an infrared absorption characteristic close to the ideal; an optical density for a 1.0 centimeter path of less than 0.1 at 400 nm and 0.3 at 300 nm; a refractive index at 25° C. of approximately 1.4620; and must be free of volatiles at $10^{-6}$ Torr and 22° C. or at 1 atmosphere and 37.7° C.

BRIEF DESCRIPTION OF THE DRAWING

The single FIGURE of the drawing is a schematic diagram showing the apparatus used in carrying out the process of this invention.

SUMMARY OF THE INVENTION

It has been discovered that the bis(hydroxyalkyl)disiloxane useful as an additive or dopant in lubricants for capacitve electronic discs can be batch distilled or purified by a stripping process so that the same meets or exceeds all of the specifications and requirements for use in a capacitive electronic disc lubricant, when the temperature versus the pressure in the process is maintained so as to produce a distilland of a specified viscosity.

DETAILED DESCRIPTION OF THE INVENTION

In accordance with the process of the present invention, the feedstock or raw material, bis(hydroxyalkyl)disiloxane, is subjected to a vacuum evaporation of the light volatile materials by bringing the pressure gradually down to about $2 \times 10^{-1}$ Torr. Once the light volatiles have been removed, heat is gradually applied, so as to keep the pressure at or below $2 \times 10^{-1}$ Torr, until further volatiles have been removed. Heat is slowly applied without polymerizing the distilland until the temperature has been stabilized at approximately 135° C. When this point is reached, the pressure is further reduced and the distilland, having a viscosity of approximately 210±30 centipoise at 25° C. is collected.

If the temperature is increased too rapidly, the material will polymerize to form a room temperature vulcanizable silicone. However, the temperature must be raised to a point high enough such that the volatiles, particularly cyclic oxides, which are the major portion of the impurities, are removed. These cyclic oxides generally distill at a pressure less than $10^{-2}$ Torr and a temperature greater than or at least equal to 100° C.

Once the bulk of the low boiling materials or light volatiles have been distilled off, the temperature is very slowly increased and the pressure is very slowly reduced until the final temperature is approximately 135° C. and the final pressure is approximately $4 \times 10^{-2}$ Torr. However, it is the viscosity of the distilland that determines when the distillation is complete and this point is reached when the distilland reaches a viscosity of about 210±30 centipoise at 25° C.

The single FIGURE of the attached drawing illustrates a system 10 in which the present batch distillation or stripping purification process can be carried out. The system 10 includes a feed flask 12 which contains 3 liters of feedstock 13 or raw material and which is connected to a vacuum system 14, a pressure monitoring system 16 and a temperature monitoring system 18.

The vacuum system 14 includes a diffusion pump 20 having an internal cold trap 22 and an external cold trap 24, all for reducing the pressure on the feedstock 13 within the feed flask 12.

The pressure monitoring system 16 includes a vent 26, a capacitance manometer sensing head 28 connected to a capacitance manometer electronics unit 30, which in turn is connected to a pressure chart recorder 32, all for sensing and monitoring the pressure within feed flask 12.

The temperature monitoring system 18 includes a thermometer 34 positioned in a thermowell 35 within feed flask 12. The thermowell 35 contains a parafin oil which replicates the temperature of the feedstock 13 within the feed flask 12. The system 18 further includes a stirring device 36 to insure uniformity of the feedstock temperature, a heating mantle 38 connected to and controlled by a thermocouple controller 40, which in turn is connected to a temperature chart recorder 42, all for sensing, monitoring and controlling the temperature within feed flask 12 and of feedstock 13 contained therein.

In accordance with the process of this invention, the feedstock 13 to be purified by stripping or batch distillation is charged to the feed flask 12 and the vacuum system 14 is made operational at room temperature to remove gases in the system. The stirrer 36 is then activated, the pressure is reduced to approximately $2 \times 10^{-1}$ Torr and the temperature is gradually increased in small increments or steps up to about 135° C. while reducing and maintaining the pressure at each increment or step in the temperature increase to the approximate $2 \times 10^{-1}$ Torr level. When the temperature has reached the 135° C. point, the pressure is gradually reduced to about $4 \times 10^{-2}$ Torr or to the proper distilland viscosity, whichever is reached first. These conditions are then maintained for approximately 2 hours. The temperature is then gradually reduced to ambient while the vacuum is maintained, and thereafter the pressure is also brought to ambient condition.

The fact that the raw material or feedstock, bis(hydroxyalkyl)disiloxane, could be batch distilled or purified by stripping in accordance with the process of this invention without degradation or polymerization was unobvious and unexpected in view of the relatively high temperatures required and the number and types of impurities present. The success of the present process is attributed to the sequential and gradual increase in temperature followed by a gradual reduction or decrease of the pressure. The process of this invention, in addition to improved output, has the beneficial result that the sequence of steps is less operator dependent, substantially simpler and easier to perform than molecular distillation, thereby reducing the possibility of loss of the feedstock or raw material which is very expensive and/or loss of the purified product. In addition to the above, the present process is readily performed with ease and simplicity, and at a substantially lessened operating time, thereby resulting in a substantial cost saving in the production of the purified product such that the same can be advantageously employed as an additive or dopant in a lubricant for a capacitive electronic disc.

The following specific Examples are included in order to illustrate the invention and for comparison purposes to illustrate the improvement thereof with greater particularity. However, it is to be understood that these Examples are not intended to limit the invention in any way.

EXAMPLE I

This Example illustrates the improved purification process of this invention. A 3 liter batch or charge of the raw material or feedstock, which was prepared in accordance with Example 1 of Wang et al, copending U.S. application Ser. No. 231,859 filed Feb. 5, 1981 now U.S. Pat. No. 4,355,062, was charged to a distillation flask similar to that shown in the FIGURE of the drawing. The pressure on the raw material within the flask was gradually reduced to $2 \times 10^{-1}$ Torr at room temperature to allow outgasing of the liquid feed stock. The feedstock within the flask was then gradually heated up to about 135° C. over a period of 2½ hours in small increments or steps while reducing and maintaining the pressure at about $2 \times 10^{-1}$ Torr at each step or increment of temperature increase. Thereafter, the temperature was maintained and the pressure was further reduced to $4 \times 10^{-2}$ Torr at about 135° C. After approximately 2 hours, without change in temperature or pressure, the temperature was gradually allowed to cool to room temperature overnight. Thereafter, the pressure was gradually brought to a normal room or ambient pressure. Of the initial three liter batch of raw material or feedstock, approximately 2⅛ liters of the product were obtained. This purified additive or dopant had an infrared spectrum which matched the infrared spectrum of a control standard. Additionally, certain tests were performed on the purified distilland to determine its more important or critical physical properties. These parameters are set forth hereinbelow in Table I.

CONTROL EXAMPLE

In this Example, a charge of the feed stock or raw material used in Example I was molecularly distilled in lieu of the batch distillation or purification by stripping process of this invention and its more important properties were determined for comparison purposes with those as determined in Example I above. A charge of the raw material or feedstock used in Example I was molecularly distilled by a process and apparatus similar to that as disclosed in U.S. Pat. No. 4,275,101 to Wang et al. This process and apparatus is similar to that which has been used commercially prior to this invention and similar to that employed to molecularly distill the bis(hydroxyalkyl)disiloxane disclosed by Wang et al in copending U.S. application Ser. No. 231,859 filed Feb. 5, 1981 now U.S. Pat. No. 4,355,062. The purified product obtained from the above-referred to molecular distillation was determined to have an infrared spectrum that matched the infrared spectrum of a control standard. The important or critical physical properties of the purified distilland obtained in this Example are set forth in Table I hereinbelow.

TABLE I

| Property | Feedstock | Example I | Control Example |
|---|---|---|---|
| Viscosity (centipoise @ 25° C.) | 115 | 218 | 210 |
| Cycloalkane present (% by vol.) | 1 | 3 | 15 |
| Refractive Index (@ 25° C.) | 1.4610 | 1.4621 | 1.4620 |
| Optical Absorption (density of 1 cm path @ 300 nm) | 0.50 | 0.19 | 0.20 |
| Density (@ 25° C.) | 0.87 | 0.88 | 0.88 |
| Surface Tension (dyne/cm @ 25°C.) | 27.8 | 28.2 | 28.0 |

As can be readily seen from a comparison of the data set forth in Table I above, the improved batch distillation or purification by stripping process of this invention can produce a bis(hydroxyalkyl)disiloxane of quality equal to or better than that produced by the heretofore known and used molecular distillation process.

The above-purified bis(hydroxyalkyl)disiloxane materials may be added to the preferred video disc methyl alkyl siloxane lubricant as an additive or dopant for use in lubricating capacitive electronic discs. These compounds are added to the lubricant in varying amounts, preferably from about 10 up to about 20 percent by weight, but may be added in amounts of from about 5 percent up to about 70 percent by weight of the lubricant.

For the Examples that follow, carrier distress, which is a measure of the distortion, loss of signal, or dropout of the audio, video and color information coming from the video disc is an important factor. The carrier distress time is measured by adding the amount of time in seconds (but discounting intervals of less than 10 microseconds) during disc playback when the r.f. output of the player arm is less than 150 millivolts peak-to-peak, and the time when the r.f. output gives above 8.6 megahertz or below 3.1 megahertz in frequency, indicating a defect. Such defects are noted by the viewer as drop-outs, up to a complete loss of the picture and sound information. The present acceptable level of carrier distress for a video disc is 3 seconds in 1 hour of playback time.

EXAMPLE II

In this Example, the disiloxane obtained in Example I above (purified by the improved process of this invention) and the Control Example was dissolved in heptane form to a 0.06 percent by weight solution and mixed with a 0.06 percent by weight solution of the purified methyl alkyl siloxane lubricant as described by Wang et al in U.S. Pat. No. 4,275,101 in heptane in a ratio of 85:15 (on a weight basis) of lubricant to dopant or additive. This solution was then sprayed onto 12 video discs which were compression molded as described by Martin et al in U.S. Pat. No. 4,228,050, and which had been previously cleaned and dried by the presently known and used commercial process. These discs were compared to discs lubricated with an undoped methyl alkyl siloxane lubricant control. Carrier distress information for the initial or virgin play of these so lubricated video discs was measured and determined, and is set forth hereinbelow in Table II.

These discs were then subjected to a hot condensation stress by being placed in a chamber maintained at 95 percent relative humidity and 100° F. (37.7° C.) and held at these conditions for a period of 1 hour. Thereafter, the carrier distress for these discs was measured and determined for the first play following the stress testing. These carrier distress data are set forth hereinbelow low in Table II.

TABLE II

| | CARRIER DISTRESS (sec. per 30 min. Playback Time) | | | |
|---|---|---|---|---|
| | Initial Play | | 1st Play After Stress | |
| Sample | Median | Range | Median | Range |
| Example I | 0.16 | 0.06–0.80 | 0.22 | 0.07–0.85 |
| Control Example | 0.15 | 0.06–3.1 | 0.20 | 0.10–6.6 |
| Control (undoped) | 0.17 | 0.06–0.30 | 7.0 | 1.8–30.6 |

From a review of the data set forth in Table II, it is readily seen that the bis(hydroxyalkyl)disiloxane additive or dopant purified by the distillation process of this invention is equally as good as, if not better than, the same disiloxane purified by molecular distillation when employed as an additive or dopant in a capacitive electronic disc lubricant. Both give substantially better results than the undoped control.

What is claimed is:
1. A process for purifying a bis(hydroxyalkyl)disiloxane by batch distillation comprising the steps of:
   (a) reducing the pressure on a batch of bis(hydroxyalkyl)disiloxane feedstock at ambient temperature to $2 \times 10^{-1}$ Torr to remove low boiling volatile components absorbed and/or dissolved in said feedstock, and
   (b) gradually increasing the temperature of said feedstock to about 135° C. and in such a manner that the pressure does not increase above about $2 \times 10^{-1}$ Torr, so as to produce a distilland having a viscosity of about 210±30 centipoise at 25° C.
2. A process in accordance with claim 1 wherein said temperature increase of step (b) is carried out over a period of about 2½ hours.
3. A process in accordance with claim 1 wherein said increased temperature of about 135° C. is maintained for a period about of at least 2 hours.
4. A process in accordance with claim 1 wherein said pressure on said feedstock is further reduced to about $4 \times 10^{-2}$ Torr.
5. A process in accordance with claim 1 wherein said bis(hydroxyalkyl)disiloxane is 1,3-bis(4-hydroxybutyl)-1,3 dodecyldimethyldisiloxane.

* * * * *